United States Patent [19]
Lichenstein et al.

[11] Patent Number: 5,326,858
[45] Date of Patent: Jul. 5, 1994

[54] NUCLEIC ACID ENCODING N-ACETYLMURAMIDASE M1

[75] Inventors: Henri Lichenstein, Ventura; Keith Langley, Newbury Park; Mark Zukowski, Thousand Oaks, all of Calif.

[73] Assignee: AMGEN Inc., Thousand Oaks, Calif.

[21] Appl. No.: 921,371

[22] Filed: Jul. 28, 1992

Related U.S. Application Data

[63] Continuation of Ser. No. 421,820, Oct. 16, 1989, abandoned.

[51] Int. Cl.$^5$ .................. C07H 21/04; C12N 15/56; A61K 37/54
[52] U.S. Cl. .................. 536/23.2; 435/172.3; 435/206; 935/14; 424/94.61
[58] Field of Search .............. 435/172.3, 206; 935/14; 536/23.2

[56] References Cited

U.S. PATENT DOCUMENTS

| | | | |
|---|---|---|---|
| 3,929,579 | 12/1975 | Yoshimura et al. | 424/50 |
| 4,394,443 | 7/1983 | Weissman et al. | 435/6 |
| 4,515,891 | 5/1985 | Yokogawa et al. | 435/68.1 |
| 4,683,195 | 7/1987 | Mullis et al. | 435/6 |
| 4,683,202 | 7/1987 | Mullis et al. | 435/6 |
| 4,990,446 | 2/1991 | Oberto | 435/69.1 |

FOREIGN PATENT DOCUMENTS

| | | | |
|---|---|---|---|
| 184575 | 6/1986 | European Pat. Off. | 935/28 |

OTHER PUBLICATIONS

Young et al., PNAS USA, vol. 80 (1983) pp. 1194–1198.
Beaucage, S. L., et al., Tetrahedron Letters, 22(20:1859–1862 (1981).
Bibb, M. J., et al., Gene, 30:157–166 (1984).
Birr, E., et al., Applied Microbiology and Biotechnology, 30:358–363 (1989).
Bradford, M. M., Analytical Biochemistry, 72:248–254 (1976).
Brawner, M. E., Gene, 40:191–201 (1985).
Buttner, M. J., et al., Mol. Gen. Genet., 209:101–109 (1987).
Cromartie, W. J., et al., The Journal of Experimental Medicine, 146:1585–1602 (1977).
Enquist, L. W., et al., Dev. Ind. Microbiol., 12:225–236 (1971).
Fleming, T. J., et al., Infection and Immunity, 52:600–608 (1986).
Fouche, P. B., et al., The Journal of Biological Chemistry, 253:6787–6793 (1978).
Harada, S., et al., J. Mol. Biol., 207:851–852 (1989).
Hash, J. H., et al., The Journal of Biological Chemistry, 212(23):5586–5590 (1967).
Hopwood, D. A., et al., eds., Genetic Manipulations of Streptomyces, pp. 104–114 (1985).
Janusz, M. J., et al., J. Exp. Med., 160:1360–1374 (1984).
Jolles, P., et al., Molecular and Cellular Biochemistry, 63:165–189 (1984).
Kawata, S., et al., Agric. Biol. Chem., 47(7):1501–1508 (1983).
Kendall, K., et al., Gene, 29:315–321 (1984).
Kieser, T., et al., Gene, 65:83–91 (1988).
Laemmli, U. K., Nature, 227:680–685 (1970).

(List continued on next page.)

*Primary Examiner*—Jacqueline Stone
*Attorney, Agent, or Firm*—Marshall, O'Toole, Gerstein, Murray & Borun

[57] ABSTRACT

Disclosed are DNA sequences encoding N-acetylmuramidase M1, polypeptide products of recombinant expression of these DNA sequences, peptides whose sequences are based upon the amino acid sequences deduced from these DNA sequences, antibodies specific for such proteins and peptides, procedures for the detection and quantitation of such proteins and nucleic acids related thereto, as well as procedures relating to the development of bacteriolytic methods, therapeutic agents, and compositions utilizing N-acetylmuramidase M1.

5 Claims, 6 Drawing Sheets

OTHER PUBLICATIONS

Lehman, T. J. A., et al., Arthritis and Rheumatism, 26(10):1259–1265 (1983).
Mitchell, W. M., et al., The Journal of Biological Chemistry, 244:17–21 (1969).
Morrissey, J. H., Analytical Biochemistry, 117:307–310 (1981).
Hybridoma Technology in the Biosciences and Medicine (T. A. Springer, ed.), Plenum Press, 1985, pp. 29–36.
Saiki, R. K., et al., Science, 230:1350–1354 (1985).
Saito, H., et al., Biochimica et Biophysica Acta, 72:619–629 (1963).
Shih, J. W., et al., The Journal of Biological Chemistry, 246:994–1006 (1971).
Yokogawa, K., et al., Agr. Biol. Chem., 39:1533–1543 (1975).
Yokogawa, K., et al., Antimicrobial Agents and Chemotherapy, 6:156–165 (1974).
Yokogawa, K., et al., Agr. Biol. Chem., 36:2055–2065 (1972).

FIGURE 1A

```
    ACAGTGTGGCGGACATCAGCAACCAGCCCCACCCTCCAAGGGCATCCTGGTCCGGCTGGAGC
 1  ------------+---------+---------+---------+---------+---------+  60
    TGTCACACCGCCTGTAGTCGTTGGTCGGGGTGGGAGGTTCCCGTAGGACCAGGCCGACCTCG

ThrValTrpArgThrSerAlaThrSerProProArgAlaSerTrpSerGlyTrpSer

CCACCGGGCTGACCCTTCCGCGCCCGCCTCCGCAGGCCCCTGTGACACCACGTCACGGGGG
 61 ------------+---------+---------+---------+---------+---------+ 120
    GGTGGCCCGACTGGGAAGGCGCGGGCGGAGGCGTCCGGGGACACTGTGGTGCAGTGCCCCC

ProProAlaAspProSerAlaProAlaSerAlaGlyProCysAspThrThrSerArgGly

CCTGCTCCGTGGGCCCAGGGCCCTCCACGGGCGAAACTTTCGCCGTCCCCGGGGTGCGGA
121 ------------+---------+---------+---------+---------+---------+ 180
    GGACGAGGCACCCGGGGTCCCGGAGGTGCCCGCCTTTGAAAGCGGCAGGGCCCCACGCCT

ProAlaProTrpGlyProArgAlaSerThrAlaGluThrPheAlaValProGlyCysGly

CCGGCAGGTCAGACGCGGCCATTGCTCTAGACCGGGAGCCGGACAGATGGGTCTTTA
181 ------------+---------+---------+---------+---------+---------+ 240
    GGCCGTCCAGTCTGCGCCGGTAACGAGATCTGGCCCTCGGCTGTCTACCCAGAAAT

ProAlaGlyGlnThrArgArgHisCysSerArgProAlaGluProThrAspGlySerLeu
```

```
     CGGGGTCTACGCGCGTGCATTACTTGTGTCGTGCTCATGGGCGACCGGCCTTTCCGGGCC
241  ------------+---------+---------+---------+---------+---------+  300
     GCCCCCAGATGCGCGCACGTAATGAACACAGACGAGTACGCTGGCCGGAAAGGCCCGG

ArgGlySerThrArgValHisTyrLeuCysArgAlaHisGlyAspArgProPheArgAla  -

CCTTCGCCGGGGCAAGCACCGGTTCATTCGCGCGTTCCACGGCTACATCCCCACTCGTGC
301  ------------+---------+---------+---------+---------+---------+  360
     GGAAGCGGCCCCGTTCGTGGCCAAGTAAGCGCGCAAGGTGCCGATGTAGGGGGTGAGCACG

ProSerProGlyGlnAlaProValIleArgAlaPheHisGlyTyrIleProHisSerCys  -

CTGGAGGCAGTCATGCCCGCGTACAGCTCTCTCGCACGCCCGCCCAGACCCGCGGTC
361  ------------+---------+---------+---------+---------+---------+  420
     GACCTCCGTCAGTACGGCGCATGTCGAGAGAGCGTGCGGGCGGGTCTGGGCCAG

LeuGluAlaValMetProAlaTyrSerSerLeuAlaArgArgGlyArgArgProAlaVal  -

GTCCTCCTCGGGGTCTCGTCAGCGCCCTCACCCTGGCGCTCACCCTGGCCCACCGCC
421  ------------+---------+---------+---------+---------+---------+  480
     CAGGAGGAGCCGCCAGAGCAGTCGCGGGAGGACCGCGAGTGGGACCCGGTGGCGGGG

ValLeuLeuGlyGlyLeuValSerAlaSerLeuAlaLeuThrLeuAlaProThrAlaAla  -
```

FIGURE 1B

```
481  GCCGCGCCCCTCGCGCCCCCGCCCCGGCAAGGACGTCGGGCCCGGGCGAGGGGTACATGGGT
     ----+----+----+----+----+----+----+----+----+----+----+----+  540
     CGGCGCGGGGAGCGCGGGGGCGGGGCCGTTCCTGCAGCCCGGGCCCGCTCCGCATGTACCCA

AlaAlaProLeuAlaProProGlyLysAspValGlyProGlyGluAlaTyrMetGly  -

541  GTCGGCACCCGCATCGAGCAGGGGCTCGGGGCTGTCCAGGGCACGAGGCACCATCGGCCCG
     ----+----+----+----+----+----+----+----+----+----+----+----+  600
     CAGCCGTGGGCGTAGCTCGTCCCCGAGCCCCGACAGGTCCCGTGCTCCGTGGTAGCCGGGC

ValGlyThrArgIleGluGlnGlyLeuGlyAlaValGlnGlyThrArgThrIleGlyPro  -

601  GCCGACACCAGCGGTGTCCAGGGGATCGACGTGTCGCACTGGCAGGGCTCCATCAACTGG
     ----+----+----+----+----+----+----+----+----+----+----+----+  660
     CGGCTGTGGTCGCCACAGGTCCCCTAGCTGCACAGCGTGACCGTCCCGAGGTAGTTGACC

AlaAspThrSerGlyValGlnGlyIleAspValSerHisTrpGlnGlySerIleAsnTrp  -

661  AGCTCGGGTGAAGTCGGGCCCGGGATGTCCTTCGCCTACATCAAGGCGACCGAGGGCACCAAC
     ----+----+----+----+----+----+----+----+----+----+----+----+  720
     TCGAGCCCACTTCAGCCCGGGCCCCTACAGGAAGCGGATGTAGTTCCGCTGGCTCCCGTGGTTG

SerSerValLysSerAlaGlyMetSerPheAlaTyrIleLysAlaThrGluGlyThrAsn  -
```

FIGURE 1C

```
      TACAAGGACGACCGGTTCAGGCGCGAACTACACCAACGCGTACAACGCGGGGATCATCCGG
      ----+----+----+----+----+----+----+----+----+----+----+----+  780
      ATGTTCCTGCTGGCCAAGTCGCGCTTGATGTGGTTGCGCATGTTGCGCCCCTAGTAGGCC
721
      TyrLysAspAspArgPheSerAlaAsnTyrThrAsnAlaTyrAsnAlaGlyIleIleArg  -

GGCGCCTACCACTTCGCGCCCGAACGCCTTCCAGCGGCACGGGCCAGGGCCGACTACTTC
      ----+----+----+----+----+----+----+----+----+----+----+----+  840
      CCGCGGATGGTGAAGCGCGGGCTTGCGGAAGGTCGCCCGTGCCCGGTCCGGCTGATGAAG
781
      GlyAlaTyrHisPheAlaArgProAsnAlaArgProAsnAlaSerSerGlyThrAlaGlnAlaAspTyrPhe  -

GCCAGCAACGGGCGGGCTGGTCCCGCGACAACCGGACCCTGCCGGGCGTCCTGGACATC
      ----+----+----+----+----+----+----+----+----+----+----+----+  900
      CGGTCGTTGCCCGCCCGACCAGGGCGCTGTTGGCCTGGGACGGCCCGCAGGACCTGTAG
841
      AlaSerAsnGlyGlyTrpSerArgAspAsnArgThrLeuProGlyValLeuAspIle  -

GAGCACAACCCCTCCGGCGCCATGTGCTACGGGCTCTCTCCACCACGCAGATGCGCACCTGG
      ----+----+----+----+----+----+----+----+----+----+----+----+  960
      CTCGTGTTGGGGAGGCCGGTACACGATGCCCGAGAGAGGTGGTGCTGTCTACGCGTGGACC
901
      GluHisAsnProSerGlyAlaMetCysTyrGlyLeuSerThrThrGlnMetArgThrTrp  -
```

FIGURE 1D

```
961   ATCAACGACTTCCACGCCCGGTACAAGGGCGGCACCACCCGCGACGTCGTCATCTACACC
      ----+----+----+----+----+----+----+----+----+----+----+----+  1020
      TAGTTGCTGAAGGTGCGGGCCATGTTCCCGCCGTGGTGGGCGCTGCAGCAGTAGATGTGG
       IleAsnAspPheHisAlaArgTyrLysAlaArgThrThrArgAspValValIleTyrThr

1021  ACGGCGAGCTGGTGGAACACCTGCACCGGCAGCTGGAACGGGCATGGGCGGCCAAGTCCCCG
      ----+----+----+----+----+----+----+----+----+----+----+----+  1080
      TGCCGCTCGACCACCTTGTGGACGTGGCCGTCGACCTTGCCGTACCCGCCGGTTCAGGGGC
       ThrAlaSerTrpTrpAsnThrCysThrGlySerTrpAsnGlyMetAlaAlaLysSerPro

1081  TTCTGGGTGGCCCACTGGGCGTGAGCGCCCCGACGGTGCCGAGCGCTTCCCGACCTGG
      ----+----+----+----+----+----+----+----+----+----+----+----+  1140
      AAGACCCACCGGGTGACCCCGCACTCGCGGGGCTGCCACGGCTCGCCGAAGGGCTGGACC
       PheTrpValAlaHisTrpGlyValSerAlaProThrValProSerGlyPheProThrTrp

1141  ACGTTCTGGCAGTACTCGGCGACCGGCAGCCGGGTCGGCGGGACGTCGACCGC
      ----+----+----+----+----+----+----+----+----+----+----+----+  1200
      TGCAAGACCGTCATGAGCCGCTGGCCGTCGGCCCAGCCGCAGTCGCCCTGCAGCTGGCG
       ThrPheTrpGlnTyrSerAlaThrGlyArgValGlyGlyValSerGlyAspValAspArg
```

FIGURE 1E

```
1201  AACAAGTTCAACGGCTCCGCCGCCCGTCTGCTGGCCCTGGCCAACAACACGGGCGTGAGAC
      ----+----+----+----+----+----+----+----+----+----+----+----+  1260
      TTGTTCAAGTTGCCGAGGCGGCGGGCAGAGACGACGGGACCGGGACCGGTTGTTGTGCCGCACTCTG

AsnLysPheAsnGlySerAlaAlaArgLeuLeuAlaLeuAlaAsnAsnThrAlaEndAsp  -

1261  GGCCCGGAGGGCCGGGGGCACGGCACGCCCTGCCCCGGCCCTCCCCGGCCCCGGC
      ----+----+----+----+----+----+----+----+----+----+----+----+  1320
      CCGGGCCTCCCGGCCCCCCGTGCCGTGCGGGACGGGGCCGGGAGGGGCGGGGCCCG

GlyArgArgAlaGlyGlyThrAlaArgThrProCysProArgProSerProAlaProGly  -

1321  GCGGGCTACCGCATCCGCTGGGCTGCTCGCGCA
      ----+----+----+-----  1353
      CGCCGATGGCGTAGGCGTCCCACGAGCGCGT

AlaAlaThrAlaSerAlaArgGlyAlaArgAla  -
```

FIGURE 1F

NUCLEIC ACID ENCODING N-ACETYLMURAMIDASE M1

This application is a continuation of application Ser. No. 07/421,820, filed Oct. 16, 1989 now abandoned.

BACKGROUND OF THE INVENTION

The present invention relates generally to N-acetylmuramidase M1 and more particularly to microbial N-acetylmuramidase M1, to DNA sequences encoding N-acetylmuramidase M1, to the polypeptide products of recombinant expression of these DNA sequences, to peptides whose sequences are based upon the amino acid sequences deduced from these DNA sequences, to antibodies specific for such proteins and peptides, to procedures for the detection and quantitation of such proteins and nucleic acids related thereto, as well as to procedures relating to the development of therapeutic agents utilizing N-acetylmuramidase M1.

The occurrence of bacteriolytic enzymes in animals, plants, and microorganisms is widespread. These enzymes are categorized into three classes based on their mechanism of action on the carbohydrate polymers, such as peptidoglycans, comprising bacterial cell walls. One class of enzyme, the glycosidases, degrades cell walls by acting on the linear sequence of N-acetyl-D-glucosamine and N-acetyl muramic acid residues. A second class, the endopeptidases, splits bonds within peptides and cross linkages between peptides. A third class, the amidases, hydrolyzes linkages between the glycan and peptide moieties.

Those glycosidases that hydrolyze the β-1,4-glycosidic bonds in the polysaccharide backbone of peptidoglycans are known as lysozymes (β-1,4-N-acetylmuramidases). Lysozymes from a variety of sources, including animal, plant, and microbial, are classified into four distinct types on the basis of the homology of their amino acid sequence: i) chicken, ii) phage, iii) goose, and iv) fungal (*Chalaropsis*). see, Jolles, *et al., Molec. Cell. Biochem.*, 63:165–189 (1984). There is no obvious sequence homology between one class of lysozymes and another class although X-ray structure analyses have shown that the three-dimensional structures of the first three types are similar to one another.

The bacterium *Streptomyces globisporus* produces two kinds of lysozyme, M1 and M2. Using the culture liltrate of *S. globisporus*, Yokogawa, K., *et al.*, in *Antimicrob. Ag. Chemother.*, 6:156 (1974), and Yokagawa, *et al.*, in *Agr. Biol. Chem.*, 39:1533 (1975), described the purification of mutanolysin, which contains multiple enzymatic activities including M1 and M2. Both M1 and M2 were found to be N-acetylmuramidases. However, the M1 enzyme (MW-20,000) was noted to show a greater lyric specificity towards *Streptococcus mutans* cell walls than the M2 enzyme (MW11,000). M1 and M2 also differ from each other in amino acid composition, immunological properties, and modes of lytic action. Kawata, S., *et al., Agric. Biol. Chem.*, 47:1501 (1983). The hydrolyzing action of M1 (composed of 186 amino acid residues) is independent of the presence of O-acetyl groups on muramic acid residues in the peptidoglycan moiety, while the action of M2 (composed of 99 amino acid residues) is suppressed by the presence of such groups. Thus, M1 is more similar to the *Chalaropsis* type lysozyme class in that both enzymes have N,O-diacetylmuramidase activity. M2 is more similar to the chicken type lysozyme class in that both enzymes cannot efficiently lyse O-acetylated peptidoglycan. Neither M1 nor M2 has been sequenced nor has the gene for either enzyme been isolated. Only preliminary X-ray crystallographic information is available and only for the M1 lysozyme. Harada, *et al., J. Mol. Biol.*, 207:851–852 (1989). The only described attempts to isolate the gene for a B-1,4-Nacetylmuramidase from *Streptomyces* has been by Birr, E., *et al., Appl. Microbiol. Biotechnol.*, 30:358 (1989). Lysozyme deficient mutants of *Streptomyces coelicolor* "Muller" were generated and then transformed with wild type *S. coelicolor* "Muller" genomic DNA. A 2.9 kb insert was identified and shown to restore lysozyme production in the mutants. However, there was no evidence demonstrating whether the 2.9 kb insert contained a structural gene for lysozyme.

N-acetylmuramidase M1 has a broad spectrum bacteriolytic activity and is particularly efficient in lysing lysozyme-resistant bacteria, such as *Streptococcus* and *Lactobacillus*. Evidence implicating involvement of lysozyme-resistant peptidoglycans in the induction of inflammatory arthritis suggests that an agent capable of lysing such resistant peptidoglycans, such as N-acetylmuramidase M1, can be an effective agent against arthritis. Bacterial cell wall peptidoglycans (particularly those which are lysozyme-resistant) are potent stimulators of inflammatory and immunologic processes. For example, when the lysozyme-resistant peptidoglycan-polysaccharide complex (PG-PS) from group A *Streptococci* or *Lactobacillus casei* is injected into experimental animals, an inflammatory arthritis develops which closely parallels the syndrome observed in humans. Cromartie, *et al., J. Exp. Med.*, 146:1585 (1977) and Lehman, *et al., Arthritis Rheum.*, 26:1259 (1983). The severity of the disease appears to be directly proportional to the dose of PG-PS that is injected. It has also been demonstrated that rats which are injected with lysozyme-resistant O-acetylated peptidoglycans from *Neisseria gonorrhea* develop a severe arthritis. However, if the experiment is repeated using lysozyme-sensitive 0-acetylation-deficient peptidoglycan from *Neisseria gonorrhea*, there is a significant reduction in the inflammatory response. Fleming, *et al., Infect. Immun.*, 52:600–608 (1986).

More recently, N-acetylmuramidase M1 has been shown to be effective in treating the arthritis that is caused by injecting group A *Streptococcal* PG-PS into rats. This arthritis manifests itself as an acute joint inflammation followed by a chronic recurrent erosive arthritis. N-acetylmuramidase M1 injected up to 3 days (approximately the time for peak acute inflammation) after the injection of group A *streptococcal* PG-PS results in a complete resolution of the acute arthritis, as well as the prevention of chronic joint disease. Furthermore, when the injection of N-acetylmuramidase M1 is delayed until 14 days (approximately the time when the chronic phase of arthritis begins) after the injection of PG-PS the severity of chronic inflammation still can be significantly reduced. Janusz, *et al., J. Exp. Med.*, 160:1360–1374 (1984).

The ability of N-acetylmuramidase M1 to be used in the treatment of human arthritis depends upon whether lysozyme-resistant peptidoglycans play a role in initiating the human arthritic condition. It is known that numerous bacteria colonize the human gastrointestinal tract. During the life cycle of these bacteria, numerous cell wall components are generated which may localize in joint and synovial tissues. The arthropathic potential of microbial components in humans is apparent in that many gastrointestinal, genito-urinary, and skin infections have an associated inflammatory arthritis.

N-acetylmuramidase M1 has also been shown to be effective in lysing many strains of cariogenic bacteria which induce dental plaque and caries. Yokogawa, et al., Agr. Biol. Chem., 39:1533-1543 (1975). Thus, N-acetylmuramidase M1 could be incorporated into chewing gum, toothpaste or mouthwash for the treatment and prevention of dental caries. While a similar idea was proposed by Yokogawa, et al., Agr. Biol. Chem., 36:2055-2065 (1972) and Yoshimura, et al., U.S. Pat. No. 3,929,579 (1975), these investigators proposed that mutanolysin (a mixture of bacteriolytic enzymes from S. globisporus, including N-acetylmuramidase M1) would be used as the preventative agent against tooth decay.

The use of N-acetylmuramidase M1 to attack cariogenic bacteria would appear to have significant advantages over using traditional oral administration of antibiotics to eliminate these bacteria. One advantage is that once ingested, N-acetylmuramidase M1 is degraded by enzymes in the stomach; the enzyme does not circulate systemically the way an antibiotic does. Another advantage of using N-acetylmuramidase M1 is that the enzyme has a bacteriocidal activity, rather than the bacteriostatic activity found with certain antibiotics. Furthermore, many cariogenic bacteria have developed resistances to antibiotics, whereas there have not been any reported instances of cariogenic bacteria that are resistant to the action of N-acetylmuramidase M1.

N-acetylmuramidase M1 could be used in other pharmaceutical or industrial applications where it is beneficial to lyse bacteria that are sensitive to this enzyme. Thus, throat lozenges could contain N-acetylmuramidase M1 to prevent and treat throat infections. N-acetylmuramidase M1 could also be formulated into ointments or creams to combat skin infections. Finally, N-acetylmuramidase M1 could be used as a preservative for foods, pharmaceuticals, cosmetics or any other products susceptible to microbial decay. Currently most products are preserved using chemicals. N-acetylmuramidase M1 would have the advantage of serving as a natural preservative that is not toxic to humans or to the environment.

Clearly, because of its broader spectrum bacteriolytic activity, N-acetylmuramidase M1 has multiple uses as a therapeutic agent requiring bacteriolytic activity. However, to date no one has developed methods for producing isolated and purified N-acetylmuramidase M1 in substantial quantities via recombinant DNA technology. Thus, there continues to exist a need in the art for such methods. To date no one has provided the amino acid sequence for N-acetyl muramidase M1, nor the DNA sequence encoding the protein. The availability of DNA sequences encoding Nacetylmuramidase M1 would make possible the application of recombinant methods to the large-scale production of this protein in procaryotic and/or eucaryotic host cells, as well as DNA-DNA, DNA-RNA, and RNA-RNA hybridization procedures for the detection, quantification and/or isolation of nucleic acids associated with this protein. Possession of the protein, and/or knowledge of the amino acid sequence of this protein, would make possible, in turn, the development of monoclonal and polyclonal antibodies thereto (including antibodies to protein fragments or synthetic peptides modelled thereon) for the use in immunological methods for the detection and quantification of the protein as well as homologous proteins, in samples, as well as allowing the development of procedures relating to the development of therapeutic agents utilizing N-acetylmuramidase M1. Knowledge of the amino acid sequence of N-acetylmuramidase M1 would also make possible the application of techniques described as protein engineering, whereby the properties of the enzyme may be altered by changing DNA codons for specific amino acids of the enzyme. Thus, the stability, activity, effective pH range, temperature range, and the like of the enzyme may be altered to impart new and improved properties.

BRIEF SUMMARY OF THE INVENTION

The present invention relates generally to N-acetylmuramidase M1 and more particularly to microbial N-acetylmuramidase M1, to DNA sequences encoding Nacetylmuramidase M1, to the polypeptide products of recombinant expression of these DNA sequences, to peptides whose sequences are based upon the amino acid sequences deduced from these DNA sequences, to antibodies specific for such proteins and peptides, to procedures for the detection and quantitation of such proteins and nucleic acids related thereto, as well as to procedures relating to the development of therapeutic agents and pharmaceutical compositions utilizing N-acetylmuramidase M1.

In presently preferred forms, novel DNA sequences comprise DNA sequences encoding N-acetyl muramidase M1 protein. Specifically, this sequence is contained in the plasmid designated pMUT-1, and deposited on Oct. 12, 1989 with the American Type Culture Collection, 12301 Parklawn Drive, Rockville, Ma. 20852, in accordance with the U.S. Patent and Trademark Office's requirements for microorganism deposits, under Accession No. 68112. Alternate DNA forms, prepared by partial or total chemical synthesis from nucleotides, as well as DNA forms encoding addition, deletion, and substitution analog polypeptides, is also included within the scope of the invention.

Association of DNA sequences provided by the invention with homologous or heterologous species expression control DNA sequences, such as promoters, operators, regulators, and the like, allows for in vitro transcription to form mRNA which, in turn, is susceptible to translation to provide N-acetyl muramidase M1 proteins, and related poly- and oligopeptides in large quantities.

Also included within the invention is the incorporation of DNA sequences into procaryotic and eucaryotic host cells by standard transformation and transfection processes, potentially involving suitable vital and circular DNA plasmid vectors, providing for useful proteins in quantities heretofore unavailable from natural sources.

In a presently preferred DNA expression system of the invention, N-acetylmuramidase M1 encoding DNA is ligated to a fragment from plasmid pIJ699 and the resulting plasmid, designated pHL47, is used to transform Streptomyces lividans TK24 allowing for the production of a functional N-acetylmuramidase M1 protein, demonstrating functional characteristics of native N-acetylmuramidase M1 including for example, cross-reactivity with anti-serum to N-acetylmuramidase and β-1,4-N-acetylmuramidase activity in lysing Micrococcus luteus.

In another presently preferred DNA expression 20 system of the invention, N-acetylmuramidase M1 encoding DNA is fused to the Streptomyces coelicolor agarase promoter and signal sequence from plasmid pIJ2002, and the resulting plasmid, designated pLBS10 is used to transform *S. lividans* TK24 thereby allowing for transcription and translation to provide N-acetylmuramidase M1.

In yet another presently preferred DNA expression system of the invention, N-acetylmuramidase M1 encoding DNA is ligated to a fragment from plasmid pCFM1156 for expression in *Escherichia coli* allowing for transcription and translation to provide a functional 27-28 kD N-acetylmuramidase M1 protein demonstrating functional characteristics of native N-acetylmuramidase M1 including for example, cross-reactivity with anti-serum to N-acetylmuramidase and β-1,4-N-acetylmuramidase activity in lysing *Micrgcoccus luteus*.

Novel protein products of the invention include polypeptides having the primary structural conformation (i.e., amino acid sequence) of N-acetylmuramidase M1 protein, as set forth in FIG. 1, as well as peptide fragments thereof and synthetic peptides assembled to be duplicative of amino acid sequences thereof. Proteins, protein fragments, and synthetic peptides of the invention are projected to have numerous uses including therapeutic uses and provides the basis for preparation of monoclonal and polyclonal antibodies specifically immunoreactive with N-acetylmuramidase M1. Antibodies of the invention can be used for affinity purification of N-acetylmuramidase M1 from other sources and cell types.

The present invention also provides for procedures for the detection and/or quantification of normal, abnormal, or mutated forms, of N-acetylmuramidase M1 as well as nucleic acids (e.g., DNA and mRNA) associated therewith. Illustratively, antibodies of the invention are employed in known immunological procedures for quantitative detection of N-acetylmuramidase M1 proteins in samples, detection of DNA sequences of the invention (particularly those having sequences encoding N-acetylmuramidase M1) that may be suitably labelled and employed for quantitative detection of mRNA encoding these proteins.

Among the multiple aspects of the present invention, therefore, is the provision of novel purified and isolated DNA sequences coding for expression of polypeptides having the biological activity of N-acetylmuramidase M1 (characterized by having β-4,N-acetylmuramidase activity) and including: (a) novel N-acetylmuramidase M1 encoding DNA sequences set out in FIG. 1, as well as (b) DNA sequences which hybridize thereto under stringent hybridization conditions, i.e., of a stringency equal to or greater than the conditions described herein and employed in the initial isolation of DNAs of the invention, and (c) DNA sequences encoding the same, allelic variant, or analog N-acetylmuramidase M1 protein or polypeptide fragments, through use of, at least in part, degenerate codohs. Correspondingly provided are vital or circular plasmid DNA vectors incorporating such DNA sequences in procaryotic and eucaryotic host cells transformed or transfected with such DNA sequences and vectors, as well as novel methods for the recombinant production of N-acetylmuramidase M1 through cultured growth of such hosts and isolation of these proteins from the hosts or their culture media. Also, the N-acetylmuramidase M1 DNA can be used as a probe in the detection and isolation of variants of N-acetylmuramidase M1 proteins and analogs thereto.

Bacteriolytic methods, therapeutic procedures, and pharmaceutical compositions which utilize N-acetylmuramidase M1 are also provided.

Other aspects and advantages of the present invention will be apparent upon consideration of the following detailed description thereof which includes numerous illustrative examples of the practice of the invention, reference being made to the drawing wherein:

FIG. 1 provides a 1353 base pair nucleotide DNA sequence and the deduced sequence of 217 amino acid residues for N-acetylmuramidase M1 having a calculated molecular weight of 23,606 daltons.

DETAILED DESCRIPTION

The following examples illustrate practice of the invention.

Example 1 relates to the generation of rabbit polyclonal antisera to N-acetylmuramidase M1.

Example 2 relates to the purification of N-acetylmuramidase M1 from *S. globisporus*.

Example 3 relates to the N-terminal amino acid sequencing of N-acetylmuramidase M1.

Example 4 relates to a determination of the amino acid sequence of a tryptic fragment from N-acetylmuramidase M1.

Example 5 relates to a determination of the design and synthesis of a probe for detection of the gene for N-acetylmuramidase M1.

Example 6 relates to a determination of the construction of the genomic library and isolation of the gene for N-acetylmuramidase M1.

Example 7 relates to a determination of the characterization of the gene for N-acetylmuramidase M1.

Example 8 relates to a determination of the expression of N-acetylmuramidase M1 in *S. lividans*.

Example 9 relates to expression of N-acetylmuramidase M1 in *S. lividans* using promoter and signal sequences from *S. coelicolor* agarase gene.

Example 10 relates to expression of N-acetylmuramidase M1 in *E. coli*.

Example 11 relates to therapeutic procedures utilizing N-acetylmuramidase M1.

Example 12 relates to the use of N-acetylmuramidase M1 DNA as probes.

The examples which follow are for illustrative purposes only and are not intended in any way to limit the scope of the invention.

EXAMPLE 1

Generation of rabbit polyclonal antisera to N-acetylmuramidase M1

Rabbit polyclonal antisera was generated from N-acetylmuramidase M1 obtained from Seikagaku Kogyo, Co., Ltd. The protein was dissolved in 0.1% sodium dodecyl sulfate (SDS) and heated for 30 min at 60° C. This preparation was injected into 3 New Zealand white rabbits (5-8 lb initial weight). Each rabbit was immunized on Day 1 with 50 μg N-acetylmuramidase M1 emulsified in an equal volume of Freund's complete adjuvant. A total volume of not more than 2 ml (1:1 Nacetylmuramidase M1:adjuvant per rabbit) was injected subcutaneously into at least 6 sites along the hindquarters. Further boosts (Days 7, 21, 35, 56) were performed by the same procedure, with the substitution of Freund's incomplete adjuvant.

Rabbits were bled by ear vein puncture on the day before the first injection (pre-immune serum) and on Days 28 and 63. Blood was collected into vacuum tubes and allowed to clot for 16 hrs at room temperature. The clot was removed and the serum spun for 10 min at 2200 rpm to remove any remaining blood cells. Serum was poured into glass vials and sodium azide added to a final concentration of 0.01%. Serum was aliquotted into polypropylene tubes and stored at −20° C.

Serum was titered using a solid-phase radioimmunoassay [*Selected Methods in Cellular Immunology*, (B. B. Mishel and S. M. Shiigi, eds.), Freeman, San Francisco, 1980, pp. 373-397 and *Hybridoma Technology in the Biosciences and Medicine* (T. A. Springer, ed.), Plenum Press, 1985, pp. 29-36]. N-acetylmuramidase M1 diluted to 0.5 µg/50 µl in carbonate-bicarbonate buffer, pH 9.2, and incubated for 2 hrs at room temperature in polystyrene wells (50 µl/well). Antigen solution was decanted; wells were then filled with 5% bovine serum albumin (BSA) for 30 min at room temperature to block remaining binding sites on plastic. Dilutions of rabbit serum in phosphate-buffered saline (PBS), pH 7,+1% BSA were added to wells (50 µl/well) after 5% BSA was decanted. Incubation was carried out for 2 hrs, room temperature, then wells were washed with an imidazole-buffered saline containing 0.02% Tween 20. $^{125}$I-labelled protein A (100,000 cpm/ 50 µl ) was added to wells and incubated for 30 min, room temperature, followed by a second wash. Wells were snapped apart and counted in a gamma counter. Counts versus antiserum dilution were graphed to determine 50% titer, i.e., the dilution at which the antiserum binds half of the maximum counts bound.

EXAMPLE 2

Purification of N-acetylmuramidase M1 from *S. globisporus*

N-acetylmuramidase M1 was purified from *S. globisporus* (A.T.C.C. #21553) to obtain material sufficiently pure for N-terminal amino acid analysis. The steps used in the purification are as follows.

A. Sephacryl S-200 gel filtration

Phenylmethylsulfonyl fluoride was added to 1855 ml of cell-free broth from the fermentation of *S. globisporus* to give a final concentration of 1 mM. After centrifugation at 17,000×g for 20 min to clarify, the material was concentrated to 500 ml using a Millipore Pellicon tangential flow ultrafiltration apparatus with a 10,000 molecular weight cutoff polysulfone membrane cassette (5 ft$^2$ total membrane area), further concentrated to 100 ml using an Amicon stirred cell with YM10 membrane, and again centrifuged (13,800×g; 20 min) to clarify.

The sample was applied to a Sephacryl TM S-200 (Pharmacia) gel filtration column (5×150 cm) equilibrated in phosphate-buffered saline (PBS). The flow rate was 70 ml/hr and fractions of 15 ml were collected. Fractions were analyzed by sodium dodecyl sulfate (SDS)-polyacrylamide gel electrophoresis (PAGE) according to the procedure described by Laemmli, *Nature*, 227:680-685 (1970) with silver-staining [Morrissey, *Anal. Biochem.*, 117:307-310 (1981)]or immunoblotting [Brawnet, *et al., Gene*, 40:191-201 (1985)]. SDS-PAGE was performed with a stacking gel containing 4% (w/v) acrylamide and separating gels containing 12.5% (w/v) acrylamide. Samples were always reduced with 2-mercaptoethanol prior to loading. N-acetylmuramidase M1 standard (Seikagaku Kogyo Co., Ltd.) migrated with an apparent $M_r$ of 27,000-28,000 relative to the molecular weight markers used (phosphorylase b, $M_r$ of 97,400; bovine serum albumin, $M_r$ of 66,200; ovalbumin, $M_r$ of 42,700; carbonic anhydrase, $M_r$ of 31,000; soybean trypsin inhibitor, $M_r$ of 21,500; and lysozyme, $M_r$ of 14,400). Aliquots (10 µl) from pools of five fractions (across the column elution volume range where material would be expected to elute) were analyzed by SDS-PAGE and silver staining. Protein bands were evident across fractions 55-184. By SDS-PAGE and immunoblot analysis, N-acetylmuramidase M1 was present in virtually all of these fractions, i.e., it was eluting in a fashion reflecting heterogeneity and possibly self-aggregation or aggregation with other proteins.

To overcome the apparent aggregation, gel filtration was repeated in the presence of a dissociating agent, deoxycholate. Fractions 55-219 from the preceding Sephacryl S-200 were pooled and 93% (i.e., 1020 ml) of the total pool was concentrated to 80 ml using an Amicon TM stirred cell with YM10 membrane. This sample was then dialyzed against 20 mM Tris-HCl, 100 mM NaCl, pH 8.2, and diluted with the same buffer to a volume of 100 ml. One-quarter volume (25 ml) of 10% (w/v) sodium deoxycholate dissolved in the same buffer was then added to give a sodium deoxycholate concentration of 2% (w/v). The sample was incubated at 4° C. for 3 hrs with mixing, and applied to a Sephacryl S-200 column (5×160 cm) equilibrated in 50 mM TrisHCl, 200 mMNaCl, 2% (w/v) sodium deoxycholate, pH 8.2. Fractions of 15 ml were collected at a flow rate of 70 ml/hr. Aliquots (40 µl) of pools of five fractions across the column were analyzed by SDS-PAGE and silver-staining and SDS-PAGE and immunoblotting. Fractions 125-149 contained the immunoreactive SDS-PAGE band; the pool also contained a major contaminant with a $M_r$ of approximately 35,000.

B. Mono Q anion exchange chromatography

Approximately 80% (175 ml) of the pool from gel filtration was concentrated to 50 ml using an Amicon TM stirred cell with YM10 membrane, dialyzed thoroughly against 2 l of 20 mM Tris-HCl, pH 8.2, and then against 20 mM Tris-HCl, 0.05% (w/v) sodium deoxycholate, pH 8.2. The post-dialysis volume was 70 ml, and the sample was centrifuged at 2000×g for 15 min to clarify. The supernatant from the centrifugation was applied to a Mono Q column (Pharmacia; 1 ml column volume) equilibrated in the Tris-HCl/sodium deoxycholate buffer. After sample application, a gradient from 0 to 0.5 M NaCl in the same buffer (total gradient volume 150 ml) was applied to elute bound material. Fractions of 2 ml were collected at a flow rate of 0.5 ml/min. By SDS-PAGE and silver-staining (40 µl aliquots loaded; gels run on pools of five fractions) it was apparent that most of the contaminating material had passed through the column during sample application (unbound). Material immunoreactive by SDS-PAGE followed by immunoblotting was not apparent in the unbound fractions but was apparent in fractions from two regions of the salt gradient. A relatively minor amount eluted at 75-100 mM NaCl and the majority eluted at approximately 135 mM NaCl. Fractions 19-23 of the gradient were pooled and represented highly purified N-acetylmuramidase Mi. A summary of the purification is given in Table 1 below.

TABLE 1

| | Purification of N-acetylmuramidase Ml | | |
|---|---|---|---|
| Step | Volume (ml) | Total Protein (mg) | Total N-acetyl-muramidase Ml (mg) |
| 1 Culture | 1855 | 489$^c$ | ~1$^f$ |

TABLE 1-continued

Purification of N-acetylmuramidase M1

| Step | Volume (ml) | Total Protein (mg) | Total N-acetyl-muramidase M1 (mg) |
|---|---|---|---|
| Medium | | | |
| 2. Culture medium concentrated | 101 | 550[c] | –1[f] |
| 3. Sephacryl ™ S-200 in PBS | 1125[a] | nd[d] | nd[d] |
| 4. Sephacryl ™ S-200 in Tris-HCl/sodium deoxycholate | 221[b] | 4.2[e] | nd[d] |
| 5. Mono Q | 10 | 0.2e | 0.2[e] |

[a]A portion (7%) of this pool was set aside for other uses.
[b]A portion (20%) of this pool was set aside for other uses.
[c]Determined by the method of Bradford [Anal. Biochem., 72:248-254 (1976)] using bovine serum albumin as standard.
[d]Not determined.
[e]Estimate, based on SDS-PAGE with silver staining.
[f]Estimate, based on SDS-PAGE with immunoblotting.

C. Preparation of sample for N-terminal amino acid sequencing

A portion (3.25 ml) of the pooled fractions 19-23 from Mono Q chromatography was dialyzed against 10 mM sodium phosphate, pH 8.2, concentrated to 102 μl using an Amicon Centricon 10 ultrafiltration unit, and subjected to N-terminal amino acid sequencing as described in Example 3.

EXAMPLE 3

N-terminal Amino Acid Sequencing of N-acetylmuramidase M1

The N-terminal amino acid sequence of N-acetylmuramidase M1 was determined to generate a DNA probe to detect the N-acetylmuramidase M1 gene from a library of S. globisporus DNA. N-acetylmuramidase M1, obtained as described in Example 2, was subjected to sequencing using an Applied Biosystems Protein Sequencer. The major sequence identified (with "X" indicating a questionable amino acid assignment) was the following:

1—2—3—4—5—6—7—8—9—10—11—12—13—14—15—16—17—18—19—20—21—
D—T—S—G—V—Q—G—I—D—V—S—H—W—Q—G—S—I—N—W—S—S—

22—23—24—25—26—27—28—29—30—31—32—33—34—35—36—37—38—39—40
V—K—S—A—G—M—S—F—A—Y—I—K—A—X—E—G—X—N—Y

EXAMPLE 4

Amino Acid Sequence of a Tryptic Fragment from N-acetylmuramidase M1

The amino acid sequence of a tryptic fragment of commercial N-acetylmuramidase M1 was identified to confirm cloning of the gene for N-acetylmuramidase M1. N-acetylmuramidase M1 (Seikagaku Kogyo Co., Ltd.) was treated to reduce and alkylate the cysteines; the protein was then digested with trypsin and the peptides were separated by reverse phase high performance liquid chromatography. One of the purified peptides was sequenced using an Applied Biosystems Sequencer. The major sequence identified was the following:

1—2—3—4—5—6—7—8—9—10—11—12—13—14—15—16—17—18—19—20—21
S—P—F—W—V—A—H—W—G—V—S—A—P—T—V—P—S—G—F—P—T

EXAMPLE 5

Design and Synthesis of a Probe for Detection of the Gene for N-acetylmuramidase M1

Streptomyces DNA is known to have a base composition of 73% G +C. Enquist and Bradley, Dev. Ind. Microbiol., 12:225-236 (1971). The high G+C content of the Streptocyces genome is reflected in a strong bias towards the use of codons that have either G or C in the third position. Bibb, et al., Gene, 30:157-166 (1984). The oligonucleotide probe was designed taking into account both the N-terminal amino acid sequence of N-acetylmuramidase M1 as well as the preference for codons with G or C in the third position. The sequence of the mixed 45-met oligonucleotide probe corresponds to amino acids 4-18 of N-acetylmuramidase M1 and is as follows:

```
        G    G     G          G    G
5' GG(C) GT(C) CAG GG(C) ATC GAC GT(C) TC(C) CAC TGG CAG

G     G
GG(C) TC(C) ATC AAC 3'
```

The probe was synthesized using the phosphotriester method of Beaucage, et al., Tetrahedron Letters, 22:1859-1862 ( 1981 ).

EXAMPLE 6

Construction of the Genomic Library and Isolation of the Gene for N-acetylmuramidase M1

S. globisporus chromosomal DNA was isolated using a procedure adapted from Saito, et al., Blochim. Biophys. Acta., 72:619-629 (1962). A single colony of S. globisporus (A.T.C.C. #21553) was grown in 10 ml of Luria Burtani (LB) medium overnight at 30° C. The mycelia were collected by centrifugation at 7000×g for 10 min and washed 2 times with 10% glycerol. The cell pellet was resuspended in 10 ml lysis buffer (0.15M NaCl, 0.1 M EDTA, pH 8.0, 2 mg/ml lysozyme) and incubated with shaking at 37° C. for 30 min. The mixture was frozen in a dry ice/ethanol bath and thawed slowly with the addition of 50 ml 0.1 M Tris-HCl, pH 9.0, 0.1M NaCl, 1% SDS. Proteins were removed by extracting with 50 ml phenol [saturated with TE (20 mM Tris-HCl, pH 8.0, 1 mM EDTA)]. The aqueous phase was re-extracted with 50 ml phenol/chloroform (1:1). NaCl was added to the aqueous phase to 0.5 M and the DNA was precipitated by the addition of 3 volumes of ethanol. The chromosomal DNA was recovered by spooling and then resuspended in 2 ml of TE overnight at 4° C. RNAase was added to give a final concentration of 50 μg/ml and the DNA was extracted once with phenol, twice with phenol/ chloroform, and once with chloroform. Sodium acetate was added to the final aqueous phase to a final concentration of 0.3 M and the DNA was precipitated by the addition of 3 vol ethanol. The suspension was centrifuged at 10,000 x g for 15 min and the pellet resuspended in 1 ml TE. Approximately 200 μg of S. globisporus chromosomal DNA was recovered.

Sixty μg of S. globisporus genomic DNA was partially digested with 1 unit of Sau3A (Boehringer Mannheim Biochemicals) for 10 min at 37° C. EDTA was added to a final concentration of 50 mM to stop the digestion and the DNA was extracted with phenol/chloroform. The aqueous phase was made 0.3 M in sodium acetate and the DNA was precipitated by the addition of 2 vol ethanol. DNA was recovered by centrifugation at 12,000×g for 5 min, resuspended in 500 μl TE and loaded on a 10–40% sucrose gradient according to published procedures. Current Protocols in Molecular Biology; F. Ausubel, R. Brent, R. Kingston, D. Moore, J. Seidman, J. Smith and K. Struhl, eds. Green Publishing Associates and Wiley-Interscience (1987). Sucrose gradient ultracentrifugation was carried out at 28,000 rpm for 18 hrs in a Beckman SW-28 rotor in a Beckman L8-55 ultracentrifuge. One half ml fractions were collected and DNA precipitated by the addition of 2 vol ethanol. The DNA was recovered by centrifugation at 12,000×g for 5 min and DNA from each fraction was resuspended in water. Aliquots of all fractions were electrophoresed on a 0.6% agarose gel and the DNA was visualized by staining with ethidium bromide. The fraction which contained DNA fragments ranging in molecular weight between 7-10 kb was used in subsequent cloning experiments.

Four μg of S. globisporus Sau3A DNA fragments (7-10 kb) were ligated to 1 μg of pBR322 that had been digested with BamHI and de-phosphorylated with phosphatase (New England Biolabs). The DNA was ligated in 250 μl ligase buffer (Molecular Cloning, T. Maniatis, E. Fritsch and J. Sambrook, eds. Cold Spring Harbor Laboratory, 1982) containing 1 unit T4 DNA ligase [Bethesda Research Laboratories (BRL)] for 15 hrs at 16° C. Sodium acetate was added to a final concentration of 0.3M and the DNA was precipitated by the addition of 3 vol ethanol. The DNA was recovered by centrifugation at 12,000×g for 5 min and resuspended in 20 μl water. Eight μl of ligated DNA was used to transform 400 μl of E. coli DH5α MCR competent cells (BRL) according to procedures described by BRL. The transformed cells were plated on 8 L-agar plates (150×15 mm) containing 100 μg/ml ampicillin and incubated at 37° C. for 16 hrs. This transformation yielded approximately 500 transformants per plate. Gene Screen (DuPont) membranes were cut to size and used to lift the transformants onto L-agar plates containing 12.5 μg/ml chloramphenicol. The plates were incubated for 15 hrs at 37° C. The membranes were processed for DNA denaturation and renaturation according to the procedures described for Colony/Plaque Screen (DuPont) and the membranes were then baked for 1 hr at 80° C. in a vacuum oven.

The membranes were pre-hybridized in 1x Denhardts solution with 1% SDS, 1M NaCl, 50 mM Tris-HCl, pH 7.5 for 3.5 hr at 65° C. The pre-hybridization solution was then made to a final concentration of 20 μg/ml with heat-treated salmon sperm DNA and approximately $255 \times 10^6$ cpm (2.5 pmoles) of the mixed oligomer probes representing the amino terminus (see Example 5) of N-acetylmuramidase M1 was added. Hybridization was allowed to proceed for 16 hrs at 65° C. Membranes were washed 2 times at 65° C. with 2X SSC+1% SDS for 30 min. Upon exposure of the membranes to X-ray film, 14 colonies were found to hybridize with the oligomer. These candidates underwent a second round of screening in which the isolated single positive colonies were subjected to the pre-hybridization and hybridization conditions described above. Six colonies continued to hybridize strongly with the oligomer probes. Plasmid DNA was prepared from these candidates using established procedures. Molecular Cloning, T. Maniatis, E. Fritsch and J. Sambrook, eds. Cold Spring Harbor Laboratory, (1982).

The six plasmids were digested with SalI and the restriction fragments were resolved by agarose gel electrophoresis and visualized by ethidium bromide staining and UV illumination. The restriction fragments were then transferred to GeneScreen Plus (DuPont), prehybridized, then hybridized with the mixed 45-mer oligonucleotide probe of Example 5 as described above. Although all six plasmids had different restriction patterns, for all six plasmids, an approximately 1.4 kb SalI fragment hybridized with the oligomer probes. The smallest of the 6 plasmids was chosen for further study and was designated pMut-1. This plasmid had a 9 kb insert of S. globisporus DNA. The 1.4 kb SalI fragment from pMut-1 was subcloned into bacteriophage M13 mp19 in both orientations. Single strand DNA was prepared from the phage and the 45-met oligonucleotide of Example 5 was used as a sequencing primer in sequencing reactions performed with Sequenase (United States Biochemical Corporation). The deduced amino acid sequence coded by the DNA sequence, 3' to the end of the primer, was found to match exactly with the amino acid sequence determined by protein sequencing of the purified preparation of N-acetylmuramidase. Once some partial DNA sequence(s) was obtained, additional complementary oligonucleotide primers were synthesized and used to complete sequencing of the two strands of the gene.

EXAMPLE 7

Characterization of the Gene for N-acetylmuramidase M1

The 1353 base pair DNA sequence of the SalI fragment of Example 6, including the region encoding N-acetylmuramidase M1 and its surrounding 5' and 3' regions, is shown in FIG. 1. The amino acid sequence of the mature N-acetylmuramidase M1 protein, as deduced from the nucleotide sequence, codes for a 217 residue polypeptide having a calculated molecular weight of 23,606 daltons and an estimated isoelectric point of 10.88. The amino acid sequence of the tryptic fragment of N-acetylmuramidase M1 described in Example 4 was found within this sequence (residues 158-178). In Streptomyces species, ATG, and to a lesser extent GTG codons, are used to initiate protein translation. Thus, the DNA sequence upstream of the gene for mature N-acetylmuramidase M1 was searched for the presence of inframe ATG or GTG codons. Two inframe ATG codons, shown in boxes, were found at positions −23 and −77 upstream of the first codon (doubly underscored) designated for the mature N- acetylmuramidase M1 polypeptide. The initiator codon 77 codons upstream has been estimated as the most likely start of translation as this codon is followed by a typical signal peptide sequence and other proteins secreted by Streptomyces have been found to be synthesized with an amino-terminal signal peptide. A perfect 15 bp inverted repeat (underscored) was found downstream of the TGA stop codon in the N-acetylmuramidase M1 gene. This repeat could serve to terminate transcription of this gene.

EXAMPLE 8

Expression of N-acetylmuramidase M1 in S.lividans

S. lividans TK24 (obtained from D. Hopwood, John Innes Institute) was chosen as a host to express the N-acetylmuramidase M1 gene from S. globisporus. A 5.7 kb BamHI-BglII fragment from pMut-1 containing the gene for N-acetylmuramidase M1, as well as 2.1 kb upstream sequence and 2.9 kb downstream sequence, was ligated to the 5.0 kb BglII fragment from plasmid pIJ699 (Kieser, et al., Gene, 65:83-91 (1988) [also available from the John Innes Institute; England]. The ligation mixture was transformed into S. lividans TK24 according to established procedures. Hopwood, D., et al., eds., Genetic Manipulations of Streptomyces, The John Innes Foundation (1985). The resultant plasmid was designated pHL47 and the orientation of the N-acetylmuramidase M1 gene in this plasmid is shown in FIG. 3. A derivative of pHL47 was also constructed by digesting pHL47 with KpnI, ligating and transforming TK24. The resultant plasmid pLBS12 is identical to pHL47 except that a 3.2 kb KpnI fragment from pHL47 has been deleted.

The immunoblot technique was used to demonstrate that TK24, harboring plasmid pHL47 or pLBS12, secreted N-acetylmuramidase M1. These strains, as well as a control TK24 strain harboring plasmid pIJ699, were grown for 96 hrs at 30° C. in 50 ml of liquid medium containing 2% dextrin, 0.5% HySoy (Sheffield), 0.25% polypeptone peptone (BBL), 0.5% disodium hydrogen phosphate, 0.1% potassium dihydrogen phosphate, 0.1% magnesium sulfate, 0.5% sodium chloride, 0.3% yeast extract, 0.3% malt extract, 34% sucrose and 0.0005% thiostrepton (Squibb).

After 72 hrs and 96 hrs of growth, mycelia were pelleted by centrifuging at 12,000×g for 5 min and supernatant proteins were analyzed by SDS-PAGE and immunoblotting (results not shown). The TK24 (pHL47) and TK24 (pLBS12) supernatants contained two proteins which cross-reacted with the antiserum to N-acetylmuramidase M1. One protein migrated with the N-acetylmuramidase M1 standard (27,000 to 28,000 daltons) and the other protein migrated with an apparent molecular weight of 30,000 daltons. As expected, in the control supernatant, there was no evidence of a protein which cross-reacted with the antiserum to N-acetylmuramidase M1.

The expressed protein was assayed for lytic activity as follows. Supernatants were collected from cultures after 72 and 96 hrs growth. The supernatants were dialyzed exhaustively against 0.5 mM EDTA, 1 mM Tris-Cl, pH 7.0. The supernatant proteins were then concentrated approximately 40-fold by ultrafiltration in Centricon-10 (Amicon) micro-concentrators. The equivalent of 1 ml of unconcentrated supernatant was then assayed for activity in a 1 ml reaction mixture containing 5 mM Tris-Cl, pH 7.0, 0.025% *Micrococcus lysodeikticus* (Sigma). The optical density at 600 nm wavelength (OD600 nm) was measured at the start of the reaction and then after 16 hrs incubation at 37° C. Supernatants from TK24 (pHL47) and from TK24 (pLBS12) produced a significant decrease in OD$_{600}$nm of *M. lysodeikticus* cells after 16 h which corresponds to lytic activity. The supernatant of TK24 (pIJ699) did not demonstrate lytic activity.

EXAMPLE 9

Expression of N-acetylmuramidase M1 in S. lividans Using Promoter and Signal Sequences from S. coelicolor Agarase Gene The gene coding for the agarase gene has been cloned from S. coelicolor and expressed in S. lividans. Kendall, et al., Gene, 29:315-321 (1984). As agarase is very efficiently secreted in S. lividans, the S. coelicolor agarase promoter and signal sequence may be fused to the DNA sequence coding for mature N-acetylmuramidase M1. The construction of the recombinant plasmid for secretion in S. lividans involves the following steps:

(1) Isolation of a 336 bp AvaII-PstI fragment from plasmid pIJ2002 (Buttnet, et al., Mol. Gen. Genet., 209:101-109 (1987) (available from John Innes Institute) containing 4 promoters utilized in agarase transcription as well as approximately 3/4 of the agarase signal sequence.

(2) Synthesis of an AvaII-SacI oligomer with the following sequence:

```
5' GTCCCGCACCCGCCGCTCATGCCGACACCAGCGGTGTCCAGGGGATCGA
3'     GGCGTGGGCGGCGAGTACGGCTGTGGTCGCCACAGGTCCCCTAGCT

TGTGTCGCACTGGCAGGGCTCCATCAACTGGAGCT 3'
ACACAGCGTGACCGTCCCGAGGTAGTTGACC       5'
```

This adaptor reconstructs the remaining amino acids in the agarase signal sequence and fuses them to the N-terminal amino acids of the mature N-acetylmuramidase M1 up to the SacI site in the N-acetylmuramidase M1 gene. The AvaII-SacI oligomer has one nucleotide change from the authentic sequence of the N-acetylmuramidase M1 gene. Nucleotide 630 (FIG. 1) has been changed from a C to a T to generate a ClaI site in the N-terminal region of the mature N-acetylmuramidase gene and to facilitate genetic manipulation of this gene. This nucleotide change does not alter the naturally occurring amino acid found at this position in the N-acetylmuramidase M1 protein.

(3) Creation of plasmid pLBS6 by the ligation of the fragments from steps 1 and 2 into plasmid pGEM-5Zf(+) (obtained from Promega Corporation) digested with PstI and SacI.

(4) Isolation of a 420 bp PstI-SacI fragment from pLBS6 containing the agarase promoters and signal sequence fused to the first 20 amino acids of mature N-acetylmuramidase M1. 5 (5) Isolation of a 1.2 kb SacI-KpnI fragment from pMut-1 containing the remainder of the N-acetylmuramidase M1 gene.

(6) Creation of the plasmid pLBS9 by the ligation of fragments from steps 4 and 5 into plasmid pGEM- 3Zf(+) (obtained from Promega Corporation) digested with KpnI and PstI.

(7) Isolation of a 4.2 kb HindIII-KpnI fragment from plasmid pIJ699 containing sequences allowing for plasmid replication in Streptomyces.

(8) Isolation of a 1.6 kb HindIII-KpnI fragment from pLBS9 containing the agarase promoters and signal sequence fused to mature N-acetylmuramidase M1.

(9) Creation of plasmid pLBS10 by the ligation of fragments from steps 7 and 8 after transformation into S. lividans TK24.

pLBS10 has transcription of the N-acetylmuramidase gene driven by the four agarase promoters. The agarase ribosome-binding site is utilized and translation initiates at the ATG found in the agarase signal peptide. Signal peptide processing occurs at the agarase signal peptide cleavage site and mature N-acetylmuramidase M1 is secreted by S. lividans.

EXAMPLE 10

Expression of N-acetyl muramidase M1 in E.coli

High level expression of foreign proteins in E. coli has been demonstrated with the use of plasmid pCFM1156. The plasmid pCFM1156 can be derived from the pCFM836 plasmid (described in U.S. Pat. No. 4,710,473; issued Dec. 1, 1987 and incorporated herein by reference) by destroying the two endogenous NdeI restriction sites, by end filling with T4 polymerase enzyme, followed by blunt end ligating, and substituting the small DNA sequence between the unique ClaI and KpnI restriction sites with the following oligonucleotide:

(3) Creation of plasmid pLBS7 by the ligation of fragments from steps 1 and 2 into pGEM-7Z (+) digested with KpnI and ClaI.

(4) Isolation of a 1.2 kb ClaI-KpnI fragment from pLBS7 containing the majority of the N-acetylmuramidase M1 gene.

(5) Synthesis of an NdeI-ClaI oligomer with the following sequence:

```
5' TATGGACACCAGCGGTGTTCAGGGTAT     3'
3'     ACCTGTGGTCGCCACAAGTCCCATAGC 5'
```

This oligomer changes nucleotide 618 from a C to a T and nucleotide 624 from a G to a T in the N-acetylmuramidase gene of FIG. 1. These changes alter the corresponding Streptomyces codons to codons that are preferred by E. coli.

(6) Creation of plasmid pLBS8 in E. coli FM5 (A.T.C.C. 53911) by ligation of fragments from steps 4 and 5 into plasmid pCFM1156 digested with KpnI and NdeI.

In pLBS8, transcription of the N-acetylmuramidase M1 gene is driven by the P$_L$ promoter. The synthetic ribosomal binding site is used to initiate translation of a protein identical to N-acetylmuramidase M1 with the exception of an extra methionine at the N-terminus.

SDS-PAGE with immunoblotting was used to demonstrate that FM5, harboring plasmid pLBS8, expressed N-acetylmuramidase M1. This strain, as well as a control strain of FM5 harboring plasmid pCFM1156, was grown to an OD600 nm of 0.5 in L-broth and kanamycin (20 μg/ml). An aliquot (0.4 ml) of each culture was

```
     ClaI
5'   CGATTTGATTCTAGAAGGAGGAATAACATATGGTTAACGCGTTGG
3'       TAAACTAAGATCTTCCTCCTTATTGTATACCAATTGCGCAACC

KpnI
AATTCGGTAC 3'
TTAAGC     5'
```

In the plasmid pCFM1156, foreign genes are cloned downstream of the regulated P$_L$ promoter and synthetic ribosomal binding sites. Construction of a recombinant plasmid for expression of the mature N-acetylmuramidase M1 gene in E. coli involves the following steps:

(1) Synthesis of a ClaI-SacI oligomer with the following sequence:

```
5' CGATGTTTCCCACTGGCAGGGCTCCATCAACTGGAGCT 3'
3'     TACAAAGGGTGACCGTCCCGAGGTAGTTGACC       5'
```

This oligomer reconstructs the 5' end of the mature N-acetylmuramidase gene from the genetically engineered ClaI site (see Example 9) to the SacI site in the N-acetylmuramidase gene. The ClaI-SacI oligomer has two nucleotide changes from the authentic N-acetylmuramidase gene in addition to the (C to T) change at position 630 (described in Example 9). These changes substitute a T for a G at position 633 and a C for a G at position 636 (See FIG. 1). These changes alter the corresponding Streptomyces codons to codons that are preferred by E. coli.

(2) Isolation of a 1.2 kb SaCI-KpnI fragment from pMut-1 containing the remainder of the N-acetylmuramidase gene.

removed and centrifuged at 12,000×g for 5 min. The supernatants were decanted and the pellets were solubilized in 0.61 M Tris-Cl, pH 6.8, 2% SDS, 10% glycerol and 5% 2-mercaptoethanol. The remaining culture was then incubated at 42° C. with shaking for 15 hrs so as to induce the P$_L$ promoter. Final OD600 nm was 1.4. An aliquot (0.14 ml) of each culture was then removed and the cell pellets were prepared and solubilized as described for the pre-induction samples. The four samples and commercial N-acetylmuramidase M1 were analyzed by SDS-PAGE and immunoblotting. The post-induction sample for pLBS8 in FM5 contained a protein cross-reactive with anti-serum to N-acetylmuramidase M1. The apparent molecular weight of this protein was indistinguishable from the commercial N-acetylmuramidase M1 (27-28 kD). The other three samples did not contain any protein cross-reactive with the anti-serum to N-acetylmuramidase M1.

EXAMPLE 11

Therapeutic Procedures Employing N-acetylmuramidase M1

The foregoing examples relating to methods for producing isolated and purified N-acetylmuramidase M1 in substantial quantities allows for the development of therapeutic agents utilizing N-acetylmuramidase M1. Because of its broad spectrum bacteriolytic activity, N-acetylmuramidase M1 has multiple uses as a therapeutic agent alone or in pharmaceutical or other compositions. It is expected that N-acetylmuramidase M1 can be used in the treatment of human arthritis and is also expected to find utility as a result of its effectiveness in lysing many strains of cariogenic bacteria which induce dental plaque and caries. The enzyme could be incorporated into chewing gum, toothpaste, or mouth wash for the treatment and prevention of dental caries. Also, it is expected that N-acetylmuramidase M1 could be used in other pharmaceutical or industrial applications where it is beneficial to lyse bacteria sensitive to this enzyme. For example, throat lozenges incorporating N-acetylmuramidase M1 could be used to prevent and treat throat infections. The enzyme could also be formulated into ointments or creams to combat skin infections of bacterial origin. In addition, N-acetylmuramidase M1 can find application as a preservative for foods, pharmaceuticals, cosmetics, or any other products susceptible to microbial decay.

EXAMPLE 12

Use of N-acetylmuramidase M1 DNA as Probes

Use of N-acetylmuramidase M1 DNA as a probe in the isolation, purification, and study of other N-acetylmuramidases from other organisms is contemplated. It is also anticipated that appropriate oligonucleotide fragments of N-acetylmuramidase M1 DNA can be used as primers to amplify (with specific DNA polymerases) genomic DNA, isolated, for example, from bacteria, fungi, avian, and mammalian sources. The amplified genomic DNA can then be analyzed to identify sequence variation/abnormality using the polymerase chain reaction assay. Saiki, *et al.*, Science, 230:1350 (1985). See also, Mullis, K. B., U.S. Pat. No. 4,683,202; Jul. 28, 1987; and Mullis, K. B., U.S. Pat. No. 4,683,195; Jul. 28, 1987.

For the analysis of mRNA for N-acetylmuramidase M1, or mRNA for related proteins, dot hybridization and Northern hybridization analyses could be used to characterize mRNA and N-acetylmuramidase M1 or M1-like molecules quantitatively and qualitatively. From these studies valuable information can be obtained about the number of different forms of N-acetyl muramidase genes and their expression in various cell types, e.g., bacteria, fungi, arian, and mammalian.

The foregoing illustrative examples relate generally to N-acetylmuramidase M1 and more particularly to microbial N-acetylmuramidase M1, to DNA sequences encoding N-acetylmuramidase M1, to the polypeptide products of recombinant expression of these DNA sequences, to peptides whose sequences are based upon the amino acid sequences deduced from these DNA sequences, to antibodies specific for such proteins and peptides, to procedures for the detection and quantitation of such proteins and of nucleic acids related thereto, as well as to procedures relating to the development of therapeutic agents utilizing N-acetylmuramidase M1. While the present invention has been described in terms of specific methods and compositions, it is understood that variations and modifications will occur to those skilled in the art upon consideration of the present invention.

Numerous modifications and variations in the invention as described in the above illustrative examples are expected to occur to those skilled in the art and consequently only such limitations as appear in the appended claims should be placed thereon.

Accordingly it is intended in the appended claims to cover all such equivalent variations which come within the scope of the invention as claimed.

What is claimed is:

1. A purified and isolated nucleic acid encoding the expression of a polypeptide having the biological activity of *Streptomyces globisporus* N-acetylmuramidase M1 described by a nucleotide sequence selected from the group consisting of:
   a) the nucleotide sequence as shown in FIG. 1;
   b) a nucleotide sequence which hybridizes under stringent conditions to the nucleotide sequence defined in (a); and
   c) a nucleotide sequence encoding the same polypeptide as encoded by the nucleotide sequences of (a) or (b) by means of degtenerate codons.

2. A procaryotic or eucaryotic host cell transformed or transfected with a DNA sequence according to claim 1.

3. A viral or circular DNA plasmid comprising a DNA sequence according to claim 1.

4. The plasmid according to claim 3 designated as pMut1 and corresponding to A.T.C.C. deposit No. 68112.

5. A viral or circular DNA plasmid according to claim 3 further comprising an expression control DNA sequence operatively associated with said N-acetylmuramidase M1 encoding DNA.

* * * * *

UNITED STATES PATENT AND TRADEMARK OFFICE
CERTIFICATE OF CORRECTION

PATENT NO. : 5,326,858

DATED : July 5, 1994

INVENTOR(S) : Henri Lichenstein, Keith Langley, Mark Zukowski

It is certified that error appears in the above-identified patent and that said Letters Patent is hereby corrected as shown below:

Column 1, line 32, after "peptide" delete [moleties] and substitute therefor -- moieties --.

Column 1, line 47-48, after "culture" delete [lil-trate] and substitute therefor -- filtrate --.

Column 1, line 54, after "MW" delete [-] and substitute therefore -- ~ --.

Column 1, line 55, first word delete [lyric] and substitute therefore -- lytic --; after "*Streptococcus*" delete [*mutans*] and substitute therefor --*mutants*--.

Column 1, line 56 after "MW" insert therefor -- ~ --.

Column 2, line 7, after "a" delete [B] and substitute therefor -- $\beta$ --.

Column 2, line 7, after "4-N" insert -- - --.

Column 2, line 51, after the word "A" capitalize "S" in Streptococcal.

Column 3, line 54, fifth word "Nacetylmuramidase" insert -- - -- after "N".

Column 4, line 16, first word "Nacetylmuramidase" insert -- - -- after "N".

Column 4, line 50, after "suitable" delete [vital] and substitute therefor -- viral --.

Column 4, line 65, after "expression" delete [20] therefor.

UNITED STATES PATENT AND TRADEMARK OFFICE
CERTIFICATE OF CORRECTION

PATENT NO. : 5,326,858

DATED : July 5, 1994

INVENTOR(S) : Henri Lichenstein, Kieth Langley, Mark Zukowski

It is certified that error appears in the above-identified patent and that said Letters Patent is hereby corrected as shown below:

Column 5, line 14, after "lysing" delete [*Micrgcoccus*] and substitute therefor -- *Micrococcus* --.

Column 5, line 45, after "$\beta$" insert -- 1, --

Column 5, line 55, after "degenerate" delete [codohs] and substitute therefor -- codons --.

Column 5, line 56, first word delete [vital] and substitute therefor -- viral --.

Column 6, line 59, first word "Nacetylmuramidase" insert -- - -- after "N".

Column 7, line 5, after "was" delete [tirered] and substitute therefor -- titered --.

Column 7, line 47, after "an" delete [Amicon] and substitute therefor -- Amicon™ --.

Column 7, line 49, after "Sephacryl" delete [TM] and substitute therefor --™--.

Column 7, line 59, after "blotting [" delete [Brawnet] and substitute therefor -- Brawner --.

Column 8, lines 15-16, after "an" delete [Ami-con TM] and substitute therefor --Ami-con™--.

UNITED STATES PATENT AND TRADEMARK OFFICE
CERTIFICATE OF CORRECTION

PATENT NO. : 5,326,858

DATED : July 5, 1994

INVENTOR(S) : Henri Lichenstein, Keith Langley, Mark Zukowski

It is certified that error appears in the above-identified patent and that said Letters Patent is hereby corrected as shown below:

Column 8, lines 36-37, after "an" delete [Ami-con TM] and substitute therefor -- Ami-con™ --.

Column 8, line 60, after "N-acetylmuramidase" delete [Mi.] and substitute therefor -- Ml. --.

Column 9, TABLE 1, No. 2, forth column, delete [-1f] and substitute therefor -- ~1f --.

Column 9, TABLE 1, No. 3, first column, delete [Sephacryl TM] and substitute therefor -- Sephacryl™ --.

Column 9, TABLE 1, No. 4, first column, delete [Sephacryl TM] and substitute therefore -- Sephacryl™ --.

Column 10, line 18, "Streptocyces" should be italized.

Column 10, line 25, after "45-" delete [met] and substitute therefor -- mer --.

Column 11, line 13, after "Boehringer" delete [Mannhelm] and substitute therefor -- Mannheim --.

Column 12, line 33, after "45-" delete [met] and substitute therefor -- mer --.

UNITED STATES PATENT AND TRADEMARK OFFICE
CERTIFICATE OF CORRECTION

PATENT NO.  :  5,326,858

DATED  :  July 5, 1994

INVENTOR(S)  :  Henri Lichenstein, Keith Langley, Mark Zukowski

It is certified that error appears in the above-identified patent and that said Letters Patent is hereby corrected as shown below:

Column 14, line 7, first word delete [OD600nm] and substitute therefor -- $OD_{600nm}$ --.

Column 14, line 28, after "pIJ002 (" delete [Buttnet] and substitute therefor -- Buttner --.

Column 14, line 64, after "MI." delete [5] and start new paragraph (5).

Column 15, line 57, after "the" delete [SaCl] and substitute therefor -- SacI --.

Column 15, line 64, after "to" delete [codohs] and substitute therefor -- codons --.

Column 15, line 66, after "the" delete [SaCl] and substitute therefor -- SacI --.

Column 16, line 23, after "the" delete [PL] and substitute therefor -- $P_L$ --.

UNITED STATES PATENT AND TRADEMARK OFFICE
CERTIFICATE OF CORRECTION

PATENT NO. : 5,326,858

DATED : July 5, 1994

INVENTOR(S) : Henri Lichenstein, Keith Langley, Mark Zukowski

Page 5 of 5

It is certified that error appears in the above-identified patent and that said Letters Patent is hereby corrected as shown below:

Column 16, line 31, after "an" delete [OD600nm] and substitute therefor -- $OD_{600nm}$ --

Column 18, line 2, after "fungi," delete [arian] and substitute therefor -- avian --.

Column 18, line 41, after "of" delete [degtenerate] and substitute therefor -- degenerate --.

Signed and Sealed this

Eighteenth Day of April, 1995

Attest:

BRUCE LEHMAN

*Commissioner of Patents and Trademarks*

*Attesting Officer*